(12) United States Patent
Tadao et al.

(10) Patent No.: US 10,096,781 B2
(45) Date of Patent: Oct. 9, 2018

(54) COMPOUND FOR ORGANIC PHOTOELECTRIC DEVICE AND ORGANIC PHOTOELECTRIC DEVICE, IMAGE SENSOR, AND ELECTRONIC DEVICE INCLUDING THE SAME

(71) Applicant: Samsung Electronics Co., Ltd., Suwon-si, Gyeonggi-do (KR)

(72) Inventors: Yagi Tadao, Hwaseong-si (KR); Takkyun Ro, Hwaseong-si (KR); Sakurai Rie, Suwon-si (KR); Seon-Jeong Lim, Yongin-si (KR); Yong Wan Jin, Seoul (KR); Yeong Suk Choi, Suwon-si (KR); Moon Gyu Han, Suwon-si (KR)

(73) Assignee: Samsung Electronics Co., Ltd., Gyeonggi-Do (KR)

( * ) Notice: Subject to any disclaimer, the term of this patent is extended or adjusted under 35 U.S.C. 154(b) by 154 days.

(21) Appl. No.: 14/971,279

(22) Filed: Dec. 16, 2015

(65) Prior Publication Data

US 2016/0211465 A1 Jul. 21, 2016

(30) Foreign Application Priority Data

Jan. 20, 2015 (KR) ........................ 10-2015-0009500

(51) Int. Cl.
*H01L 51/00* (2006.01)
*H01L 27/30* (2006.01)
*C07D 495/04* (2006.01)
*H01L 51/42* (2006.01)

(52) U.S. Cl.
CPC ........ *H01L 51/0071* (2013.01); *C07D 495/04* (2013.01); *H01L 27/307* (2013.01); *H01L 51/0052* (2013.01); H01L 51/0046 (2013.01); H01L 51/4253 (2013.01)

(58) Field of Classification Search
None
See application file for complete search history.

(56) References Cited

U.S. PATENT DOCUMENTS

| 8,525,577 | B2 | 9/2013 | Yofu et al. |
| 2013/0299799 | A1 | 11/2013 | Yofu et al. |

FOREIGN PATENT DOCUMENTS

| JP | 2010087405 A | 4/2010 |
| JP | 5498680 B2 | 5/2014 |
| JP | 5520560 B2 | 6/2014 |

OTHER PUBLICATIONS

CAPLUS printout of "Moghaddam, et al., A new and facile synthesis of thieno [2,3-b] indole derivatives via condensation of isocyanide and indolin-2-thiones. Synlett, 2009, (7), 1047-1050.".*

* cited by examiner

*Primary Examiner* — Po-Chih Chen
(74) *Attorney, Agent, or Firm* — Harness, Dickey & Pierce, P.L.C.

(57) ABSTRACT

A compound is selected from the compound represented by Chemical Formula 1A, the compound represented by Chemical Formula 1B, and a mixture thereof.

21 Claims, 7 Drawing Sheets

COMPOUND FOR ORGANIC PHOTOELECTRIC DEVICE AND ORGANIC PHOTOELECTRIC DEVICE, IMAGE SENSOR, AND ELECTRONIC DEVICE INCLUDING THE SAME

CROSS-REFERENCE TO RELATED APPLICATION

This application claims the benefit of priority from Korean Patent Application No. 10-2015-0009500 filed in the Korean Intellectual Property Office on Jan. 20, 2015, the entire contents of which are incorporated herein by reference.

BACKGROUND

1. Field

Example embodiments provide a compound for an organic photoelectric device, an organic photoelectric device, an image sensor, and an electronic device including the same.

2. Description of the Related Art

A photoelectric device converts light into an electrical signal using photoelectric effects, and may include a photodiode and/or a phototransistor. The photoelectric device may be applied to an image sensor, a solar cell and/or an organic light emitting diode.

An image sensor including a photodiode requires relatively high resolution and thus a relatively small pixel. At present, a silicon photodiode is widely used, but has a problem of deteriorated sensitivity because the silicon photodiode has a relatively small absorption area due to relatively small pixels. Accordingly, an organic material that is capable of replacing silicon has been researched.

The organic material has a relatively high extinction coefficient and selectively absorbs light in a particular wavelength region depending on a molecular structure, and thus may simultaneously replace a photodiode and a color filter and resultantly improve sensitivity and contribute to relatively high integration.

This organic material is used to form an active layer for an organic photoelectric device through a deposition process. When the organic material is repeatedly deposited, the organic material is decomposed and deteriorates quality of the active layer obtained after three depositions. The quality deterioration of the active layer deteriorates reliability and productivity during mass production.

SUMMARY

Example embodiments provide a compound for an organic photoelectric device that does not deteriorate quality of an active layer despite repeated deposition processes and that selectively absorbs light in a green wavelength region.

Example embodiments also provide an organic photoelectric device capable of improving reliability during mass production, selectively absorbing light in a green wavelength region, and improving efficiency.

Example embodiments also provide an image sensor and an electronic device including the compound for an organic photoelectric device.

According to example embodiments, a compound is represented by the following Chemical Formula 1A or 1B.

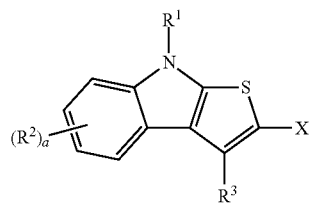

[Chemical Formula 1A]

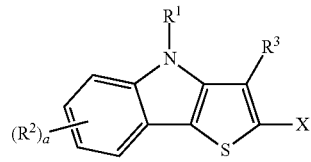

[Chemical Formula 1B]

In Chemical Formulae 1A and 1B, each of $R^1$ to $R^3$ are independently one of hydrogen and a monovalent organic group, a is an integer of 0 to 4, and X is represented by Chemical Formula 2:

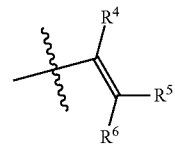

[Chemical Formula 2]

wherein, in Chemical Formula 2, $R^4$ is one of hydrogen and a monovalent organic group, and $R^5$ and $R^6$ form a heteroatom-containing ring having electron withdrawing properties.

The heteroatom-containing ring may be one of the substituents represented by the following Chemical Formulae 1a to 1e.

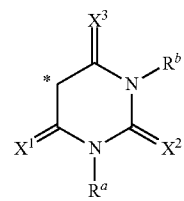

1a

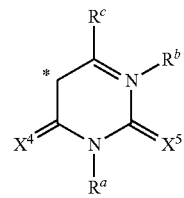

1b

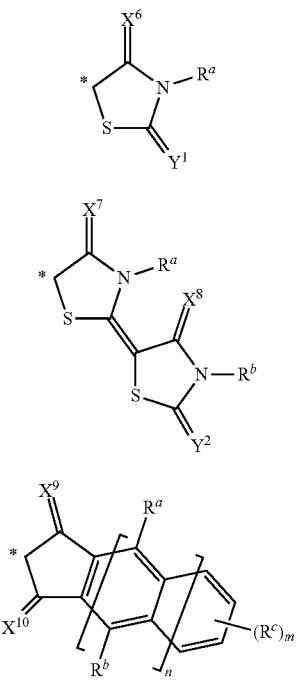

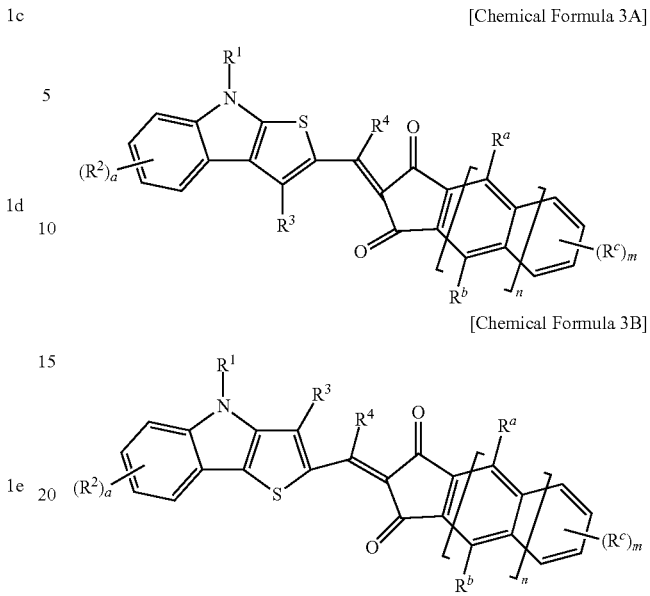

In Chemical Formulae 1a to 1e,

\* indicates a position bound to a methine group of Chemical Formula 2, each of $R^a$, $R^b$, and $R^c$ are independently one of hydrogen and a monovalent organic group, each of $X^1$ to $X^{10}$ are independently one of O and S, each of $Y^1$ and $Y^2$ are independently one of S and CRR' (wherein R and R' are independently one of hydrogen, CN, and a $C_1$ to $C_{10}$ alkyl group), m is an integer of 1 to 3, and n is an integer of 0 or 1.

In Chemical Formulae 1A, 1B, and 1a to 1e, the monovalent organic group refers to one of a substituted or unsubstituted $C_1$ to $C_{30}$ alkyl group, a substituted or unsubstituted $C_1$ to $C_{30}$ alkoxy group, a substituted or unsubstituted $C_4$ to $C_{30}$ cycloalkyl group, a substituted or unsubstituted $C_6$ to $C_{30}$ aryl group, a substituted or unsubstituted $C_3$ to $C_{30}$ heterocycloalkyl group, a substituted or unsubstituted $C_3$ to $C_{30}$ heteroaryl group, an amine group, a substituted or unsubstituted $C_1$ to $C_{30}$ alkylamine group, a substituted or unsubstituted $C_6$ to $C_{30}$ arylamine group, a substituted or unsubstituted silyl group, a substituted or unsubstituted $C_6$ to $C_{30}$ aryloxy group, a thiol group, a substituted or unsubstituted $C_1$ to $C_{30}$ alkylthio group, a substituted or unsubstituted $C_6$ to $C_{30}$ arylthio group, a cyano group, a cyano-containing group, a halogen, a halogen-containing group, a substituted or unsubstituted sulfonyl group, a substituted or unsubstituted aminosulfonyl group, a substituted or unsubstituted arylsulfonyl group, and a combination thereof.

In Chemical Formulae 1A, 1B, and 1a to 1e, the monovalent organic group may be one of a $C_1$ to $C_6$ alkyl group, a $C_1$ to $C_6$ haloalkyl group, a $C_6$ to $C_{18}$ aryl group, a halogen, a cyano group, and a cyano-containing group.

The compound for an organic photoelectric device may be represented by the following Chemical Formula 3A or 3B.

In Chemical Formulae 3A and 3B, each of $R^1$ to $R^3$ are independently one of hydrogen and a monovalent organic group, a is an integer of 0 to 4, each of $R^a$, $R^b$, and $R^c$ are independently one of hydrogen and a monovalent organic group, m is an integer of 1 to 3, and n is an integer of 0 or 1.

The compound may show a light absorption curve having a full width at half maximum (FWHM) in a thin film state of about 50 nm to about 100 nm.

The compound may have a maximum absorption wavelength ($\lambda_{max}$) at about 500 nm to about 600 nm.

The compound may be a p-type semiconductor compound.

The compound may have a higher melting point by about 50° C. or greater than a deposition temperature.

According to example embodiments, an organic photoelectric device includes a first electrode and a second electrode facing each other, and an active layer between the first electrode and the second electrode, the active layer including the compound of example embodiments.

The n-type semiconductor compound may be one of a sub-phthalocyanine, fullerene or a fullerene derivative, thiophene or a thiophene derivative, and a combination thereof.

The active layer may include the compound selected from the compound represented by Chemical Formula 1A, the compound represented by Chemical Formula 1B, and a mixture thereof.

The active layer may further include an n-type semiconductor compound.

The active layer may further include at least one of a p-type layer on one side of the intrinsic layer and an n-type layer on the other side of the intrinsic layer.

The compound may be a first p-type semiconductor compound, and the active layer may further include a second p-type semiconductor compound selectively absorbing green light.

The p-type semiconductor compound may be a compound represented by the following Chemical Formula 7.

[Chemical Formula 7]

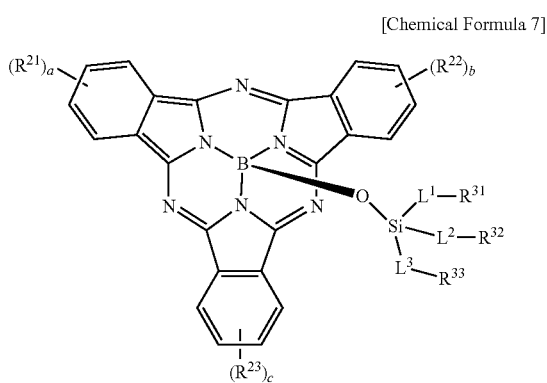

In Chemical Formula 7, each of $R^{21}$ to $R^{23}$ are independently one of hydrogen, a substituted or unsubstituted $C_1$ to $C_{30}$ alkyl group, a substituted or unsubstituted $C_1$ to $C_{30}$ alkoxy group, a substituted or unsubstituted $C_4$ to $C_{30}$ cycloalkyl group, a substituted or unsubstituted $C_6$ to $C_{30}$ aryl group, a substituted or unsubstituted $C_3$ to $C_{30}$ heterocycloalkyl group, a substituted or unsubstituted $C_3$ to $C_{30}$ heteroaryl group, an amine group, a substituted or unsubstituted $C_1$ to $C_{30}$ alkylamine group, a substituted or unsubstituted $C_6$ to $C_{30}$ arylamine group, a substituted or unsubstituted silyl group, a substituted or unsubstituted $C_1$ to $C_{30}$ aryloxy group, a substituted or unsubstituted $C_1$ to $C_{30}$ alkylthio group, a substituted or unsubstituted $C_6$ to $C_{30}$ arylthio group, a cyano group, a cyano-containing group, a halogen, a halogen-containing group, a substituted or unsubstituted sulfonyl group, a substituted or unsubstituted aminosulfonyl group, a substituted or unsubstituted arylsulfonyl group, and a combination thereof, or each of $R^{21}$ to $R^{23}$ are independently present or are fused to each other to provide a ring, each of $L^1$ to $L^3$ are independently one of a single bond, a substituted or unsubstituted $C_1$ to $C_{30}$ alkylene group, a substituted or unsubstituted $C_6$ to $C_{30}$ arylene group, a divalent substituted or unsubstituted $C_3$ to $C_{30}$ heterocyclic group, and a combination thereof, and each of $R^{31}$ to $R^{33}$ are independently one of a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heterocyclic group, a substituted or unsubstituted $C_1$ to $C_{30}$ alkoxy group, a substituted or unsubstituted amine group, a substituted or unsubstituted $C_6$ to $C_{30}$ arylamine group, a substituted or unsubstituted silyl group, and a combination thereof.

Example embodiments also provide an image sensor including the organic photoelectric device of example embodiments.

The image sensor may include a semiconductor substrate integrated with a plurality of first photo-sensing devices sensing light in a blue wavelength region and a plurality of second photo-sensing devices sensing light in a red wavelength region, and the organic photoelectric device on the semiconductor substrate and selectively absorbing light in a green wavelength region.

The first photo-sensing devices and the second photo-sensing devices may be stacked in a vertical direction on the semiconductor substrate.

The image sensor may further include a color filter layer between the semiconductor substrate and the organic photoelectric device, and the color filter includes a blue filter selectively absorbing light in a blue wavelength region and a red filter selectively absorbing light in a red wavelength region.

The organic photoelectric device may be a green photoelectric device, and the green photoelectric device, a blue photoelectric device selectively absorbing light in a blue wavelength region, and a red photoelectric device selectively absorbing light in a red wavelength region may be stacked.

According to example embodiments, an electronic device includes the image sensor of example embodiments.

DETAILED DESCRIPTION

Figure 1:
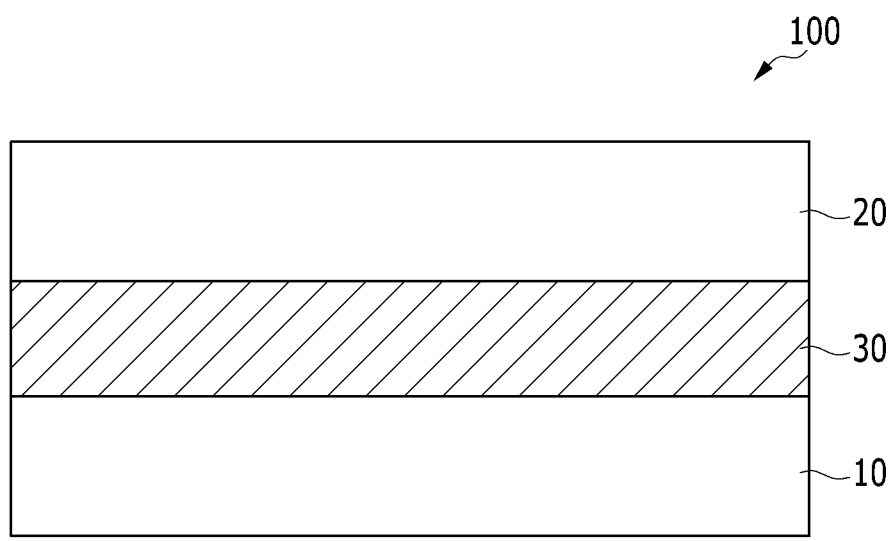
FIG. 1 is a cross-sectional view of an organic photoelectric device according to example embodiments.

Example embodiments will hereinafter be described in detail, and may be more easily performed by those who have common knowledge in the related art. However, this disclosure may be embodied in many different forms and is not construed as limited to the example embodiments set forth herein.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

In the drawings, parts having no relationship with the description are omitted for clarity of the embodiments, and the same or similar constituent elements are indicated by the same reference numerals throughout the specification.

It will be understood that when an element or layer is referred to as being "on," "connected to," "coupled to," or "covering" another element or layer, it may be directly on, connected to, coupled to, or covering the other element or layer, or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It will be understood that, although the terms first, second, third, etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the example embodiments.

Spatially relative terms, e.g., "beneath," "below," "lower," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of the example embodiments. As used herein, the singular forms "a," "an," and "the" are intended to include the plural forms as well, unless the context clearly indicates otherwise. It will be further understood that the terms "comprises," "comprising," "includes," and/or "including," if used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art. It will be further understood that terms, including those defined in commonly used dictionaries, should be interpreted as having a meaning that is consistent with their meaning in the context of the relevant art and will not be interpreted in an idealized or overly formal sense unless expressly so defined herein.

As used herein, when specific definition is not otherwise provided, the term "substituted" refers to one substituted with a substituent selected from a halogen (F, Br, Cl, or I), a nitro group, a cyano group, an amino group, an azido group, an amidino group, a hydrazino group, a hydrazono group, a carbonyl group, a carbamyl group, a thiol group, an ester group, a $C_1$ to $C_{20}$ alkyl group, a $C_1$ to $C_{20}$ alkoxy group, a $C_2$ to $C_{20}$ alkenyl group, a $C_2$ to $C_{20}$ alkynyl group, a $C_6$ to $C_{30}$ aryl group, a $C_7$ to $C_{30}$ arylalkyl group, a $C_1$ to $C_4$ alkoxy group, a $C_1$ to $C_{20}$ heteroalkyl group, a $C_3$ to $C_{20}$ heteroarylalkyl group, a $C_3$ to $C_{30}$ cycloalkyl group, a $C_3$ to $C_{15}$ cycloalkenyl group, a $C_6$ to $C_{15}$ cycloalkynyl group, a $C_2$ to $C_{20}$ heterocycloalkyl group, and a combination thereof, instead of hydrogen of a compound.

As used herein, when specific definition is not otherwise provided, the term "hetero" refers to one including 1 to 3 heteroatoms selected from N, O, S, and P.

As used herein, when a definition is not otherwise provided, the "halogen" refers to F, Cl, Br, or I, and the "haloalkyl group" refers to an alkyl group where at least one hydrogen is replaced by F, Cl, Br, or I. Examples of the haloalkyl group may be a fluoroalkyl group, for example a perfluoroalkyl group.

As used herein, when a definition is not otherwise provided, "a cyano-containing group" refers to a $C_1$ to $C_{30}$ alkyl group, a C2 to $C_{30}$ alkenyl group, or a C2 to $C_{30}$ alkynyl group where at least one hydrogen is replaced by a cyano group. Examples of the cyano-containing group may be =$CR^{x'}$—$(CR^xR^y)_p$—$CR^{y'}(CN)_2$, wherein $R^x$, $R^y$, $R^{x'}$, and $R^{y'}$ are independently hydrogen or a $C_1$ to $C_{10}$ alkyl group and p is an integer of 0 to 10. For example, the cyano-containing group may be a dicyanomethyl group, a dicyanomethenyl group, or a cyanomethynyl group.

Hereinafter, a compound for an organic photoelectric device according to example embodiments is described.

A compound for an organic photoelectric device according to example embodiments is represented by the following Chemical Formula 1A or 1B.

[Chemical Formula 1A]

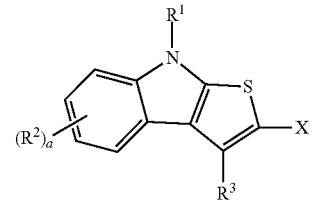

[Chemical Formula 1B]

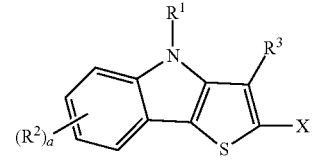

In Chemical Formulae 1A and 1B, each of $R^1$ to $R^3$ are independently one of hydrogen and a monovalent organic group, a is an integer of 0 to 4, and X is represented by Chemical Formula 2:

[Chemical Formula 2]

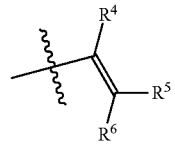

wherein, in Chemical Formula 2, $R^4$ is one of hydrogen and a monovalent organic group, and $R^5$ and $R^6$ form a heteroatom-containing ring having electron withdrawing properties.

In Chemical Formula 1A or 1B, when a is 2 or more, each $R^2$ may be different.

The heteroatom-containing ring may be one of the substituents represented by the following Chemical Formulae 1a to 1e.

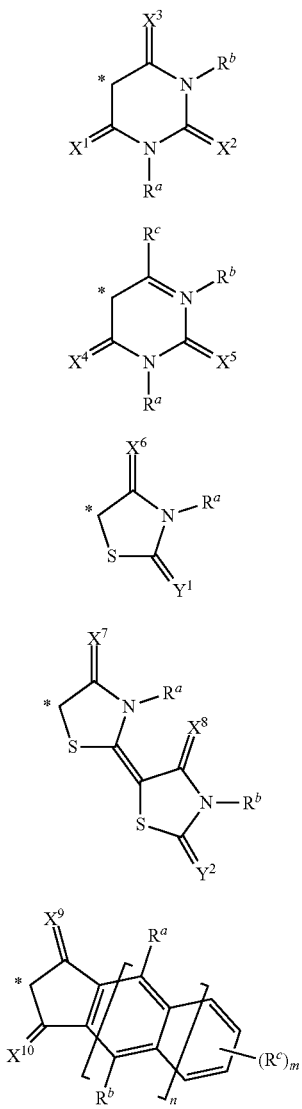

In Chemical Formulae 1a to 1e,

* indicates a position bound to a methine group of Chemical Formula 2, each of $R^a$, $R^b$, and $R^c$ are independently one of hydrogen and a monovalent organic group, each of $X^1$ to $X^{10}$ are independently one of O and S, each of $Y^1$ and $Y^2$ are independently one of S and CRR' (wherein each of R and R' are independently one of hydrogen, CN, and a $C_1$ to $C_{10}$ alkyl group), m is an integer of 1 to 3, and n is an integer of 0 or 1.

In Chemical Formulae 1A, 1B, and 1a to 1e, the monovalent organic group refers to one of a substituted or unsubstituted $C_1$ to $C_{30}$ alkyl group, a substituted or unsubstituted $C_1$ to $C_{30}$ alkoxy group, a substituted or unsubstituted $C_4$ to $C_{30}$ cycloalkyl group, a substituted or unsubstituted $C_6$ to $C_{30}$ aryl group, a substituted or unsubstituted $C_3$ to $C_{30}$ heterocycloalkyl group, a substituted or unsubstituted $C_3$ to $C_{30}$ heteroaryl group, an amine group, a substituted or unsubstituted $C_1$ to $C_{30}$ alkylamine group, a substituted or unsubstituted $C_6$ to $C_{30}$ arylamine group, a substituted or unsubstituted silyl group, a substituted or unsubstituted $C_1$ to $C_{30}$ aryloxy group, a thiol group, a substituted or unsubstituted $C_1$ to $C_{30}$ alkylthio group, a substituted or unsubstituted $C_6$ to $C_{30}$ arylthio group, a cyano group, a cyano-containing group, a halogen, a halogen-containing group, a substituted or unsubstituted sulfonyl group, a substituted or unsubstituted aminosulfonyl group, a substituted or unsubstituted arylsulfonyl group, and a combination thereof.

In Chemical Formulae 1A, 1B, and 1a to 1e, the monovalent organic group may be a substituted or unsubstituted $C_1$ to $C_6$ alkyl group, for example, one of a $C_1$ to $C_6$ haloalkyl group, a substituted or unsubstituted $C_6$ to $C_{18}$ aryl group, a halogen, a cyano group, and a cyano-containing group. In example embodiments, $R^1$ of Chemical Formula 1A and Chemical Formula 1B may be a substituted or unsubstituted $C_6$ to $C_{18}$ aryl group.

The compound includes an electron donor moiety and an electron acceptor moiety in one molecule, and thus has bipolar characteristics.

The compound has a benzopyrrolethiophene structure as the electron donor moiety, and thus a structure having improved thermal stability. As shown in examples and comparative examples described later, a compound including a benzene ring and a thiophene ring which are not bound to each other is decomposed when heated at a higher temperature than the melting point, and thus deteriorates mass productivity during the deposition. On the contrary, the compound has the electron donor moiety of a fixed molecular structure in which a benzene ring and a thiophene ring are bound to each other with pyrrole as a fixed center in the middle and a high melting point, and thus is not decomposed at a lower temperature than the deposition process. Accordingly, the compound may not deteriorate properties of a film formed through a deposition process even during the mass production deposition process, and thus has improved reliability and mass productivity.

The compound may show a light absorption curve having a relatively narrow full width at half maximum (FWHM) in a thin film state of about 50 nm to about 100 nm, for example, about 50 nm to about 90 nm. Herein, the FWHM is a width of a wavelength corresponding to half of a maximum absorption point. As used herein, when a specific definition is not otherwise provided, the FWHM may be defined by absorbance measured by UV-Vis spectroscopy. When the full width at half maximum (FWHM) is within the range, selectivity in a green wavelength region may be increased. The thin film may be a thin film deposited under a vacuum condition.

The compound is a compound selectively absorbing light in a green wavelength region, and may have a maximum absorption wavelength ($\lambda_{max}$) at about 500 nm to about 600 nm.

The compound works as a p-type semiconductor, and may be appropriately used when it has a higher LUMO level than an n-type material which is mixed therewith. For example, when the compound is mixed with fullerene as the n-type material, the compound should have a higher LUMO level than 4.2 eV which is the LUMO level of the fullerene. As for an appropriate HOMO-LUMO level, when the HOMO level is in a range of about 5.0 to about 5.8 eV and an energy bandgap ranges from about 1.9 to about 2.3 eV, the LUMO level will be in a range of about 3.9 to about 2.7 eV. The compound has a HOMO level, a LUMO level, and an energy bandgap within the ranges, and thus may be applied as a p-type semiconductor compound effectively absorbing light in a green wavelength region and having relatively high external quantum efficiency (EQE), and resultantly improves photoelectric conversion efficiency.

The compound may have a molecular weight of about 300 to about 1500, for example, about 350 to about 1200, or about 400 to about 900. When the compound has a molecular weight within the ranges, crystallinity may be effectively prevented or inhibited and thermal decomposition may also be effectively prevented or inhibited when deposited to form a thin film.

The compound has a greater than or equal to about 50° C. higher melting point than a general deposition temperature, and thus is not decomposed at a lower temperature than the deposition temperature, and resultantly, increases reliability and productivity during the mass production. The compound may have a melting point of greater than or equal to about 250° C., for example, greater than or equal to about 280° C., greater than or equal to 300° C., or greater than or equal to about 320° C. When the compound has a melting point within the ranges, the compound may be stably deposited and produce a relatively small decomposed product and thus provide an organic photoelectric device having improved photoelectric conversion performance.

Hereinafter, an organic photoelectric device including the compound according to example embodiments is described with reference to drawings.

FIG. 1 is a cross-sectional view showing an organic photoelectric device according to example embodiments.

Referring to FIG. 1, an organic photoelectric device 100 according to example embodiments includes a first electrode 10 and a second electrode 20, and an active layer 30 interposed between the first electrode 10 and the second electrode 20.

One of the first electrode 10 and the second electrode 20 is an anode and the other is a cathode. At least one of the first electrode 10 and the second electrode 20 may be a light-transmitting electrode, and the light-transmitting electrode may be made of, for example, a transparent conductor (e.g., indium tin oxide (ITO) or indium zinc oxide (IZO)), or a metal thin layer of a monolayer or multilayer. When one of the first electrode 10 and the second electrode 20 is a non-light-transmitting electrode, the first electrode 10 or the second electrode 20 may be made of, for example, an opaque conductor, for example, aluminum (Al).

The active layer 30 includes a p-type semiconductor and an n-type semiconductor to form a pn junction, and absorbs external light to generate excitons and then separates the generated excitons into holes and electrons.

The active layer 30 includes a compound selected from the compound represented by Chemical Formula 1A, the compound represented by Chemical Formula 1B, and a mixture thereof. The compound for an organic photoelectric device may act as a p-type semiconductor compound in the active layer 30.

The compound for an organic photoelectric device is a compound that selectively absorbs light in a green wavelength region, and the active layer 30 including the compound may have a maximum absorption wavelength ($\lambda_{max}$) at about 500 nm to about 600 nm.

The active layer 30 may show a light absorption curve having a relatively narrow full width at half maximum (FWHM) in a thin film state of about 50 nm to about 100 nm, for example, about 50 nm to about 90 nm. Accordingly, the active layer 30 has relatively high selectivity for light in a green wavelength region.

The active layer 30 may further include an n-type semiconductor compound for forming a pn junction.

The n-type semiconductor compound may be sub-phthalocyanine, a sub-phthalocyanine derivative, fullerene or a fullerene derivative, thiophene or a thiophene derivative, or a combination thereof.

The sub-phthalocyanine derivative may be represented by the following Chemical Formula 4.

[Chemical Formula 4]

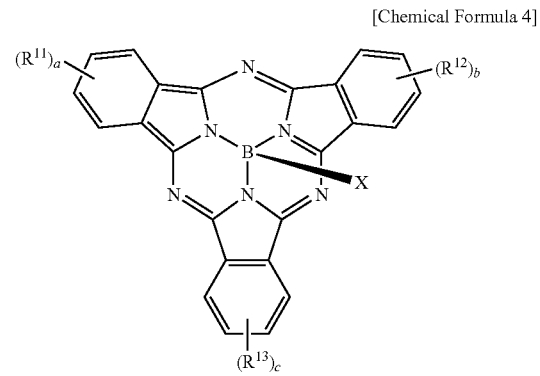

In Chemical Formula 4, each of $R^{11}$ to $R^{13}$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a halogen, a halogen-containing group, and a combination thereof, a, b, and c are integers ranging from 1 to 3, and X is a halogen, for example, F or Cl.

The halogen may refer to F, Cl, Br, or I, and the halogen-containing group may refer to a group, for example, an alkyl group where at least one hydrogen is substituted with F, Cl, Br, or I.

The thiophene derivative may be, for example, represented by the following Chemical Formula 5 or 6, but is not limited thereto.

[Chemical Formula 5]

[Chemical Formula 6]

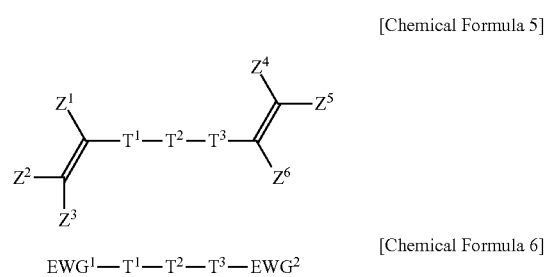

In Chemical Formulae 5 and 6, each of $T^1$, $T^2$, and $T^3$ are aromatic rings including substituted or unsubstituted thiophene moieties, each of $T^1$, $T^2$, and $T^3$ are independently present or are fused to each other, each of $Z^1$ to $Z^6$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heterocyclic group, a cyano group, and a combination thereof, and each of $EWG^1$ and $EWG^2$ are independently electron withdrawing groups.

For example, in Chemical Formula 5, at least one of $Z^1$ to $Z^6$ is an electron withdrawing group, for example, a cyano group.

The compound is a first p-type semiconductor compound, and the active layer 30 may further include a second p-type semiconductor compound selectively absorbing green light. The second p-type semiconductor compound may be a compound represented by the following Chemical Formula 7.

[Chemical Formula 7]

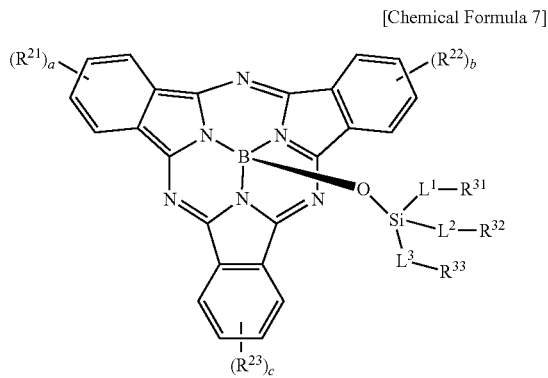

In Chemical Formula 7, each of $R^{21}$ to $R^{23}$ are independently one of hydrogen, a substituted or unsubstituted $C_1$ to $C_{30}$ aliphatic hydrocarbon group, a substituted or unsubstituted $C_6$ to $C_{30}$ aromatic hydrocarbon group, a substituted or unsubstituted $C_1$ to $C_{30}$ aliphatic heterocyclic group, a substituted or unsubstituted C2 to $C_{30}$ aromatic heterocyclic group, a substituted or unsubstituted $C_1$ to $C_{30}$ alkoxy group, a substituted or unsubstituted $C_1$ to $C_{30}$ aryloxy group, a thiol group, a substituted or unsubstituted $C_1$ to $C_{30}$alkylthio group, a substituted or unsubstituted $C_6$ to $C_{30}$ arylthio group, a cyano group, a cyano-containing group, a halogen, a halogen-containing group, a substituted or unsubstituted sulfonyl group, a substituted or unsubstituted aminosulfonyl group, a substituted or unsubstituted arylsulfonyl group, and a combination thereof, or each of $R^{21}$ to $R^{23}$ are independently present or are fused to each other to provide a ring, each of $L^1$ to $L^3$ are independently one of a single bond, a substituted or unsubstituted $C_1$ to $C_{30}$ alkylene group, a substituted or unsubstituted $C_6$ to $C_{30}$ arylene group, a divalent substituted or unsubstituted $C_3$ to $C_{30}$ heterocyclic group, and a combination thereof, and each of $R^{31}$ to $R^{33}$ are independently one of a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heterocyclic group, a substituted or unsubstituted $C_1$ to $C_{30}$ alkoxy group, a substituted or unsubstituted amine group, a substituted or unsubstituted $C_6$ to $C_{30}$ arylamine group, a substituted or unsubstituted silyl group and a combination thereof.

The second p-type semiconductor compound selectively absorbs green light, and may be included in an amount of about 500 to about 1500 parts by weight based on 100 parts by weight of the compound selected from the compound represented by Chemical Formula 1A, the compound represented by Chemical Formula 1B, and a mixture thereof.

The active layer 30 may be a single layer or a multilayer. The active layer 30 may be, for example, an intrinsic layer (I layer), a p-type layer/I layer, a I layer/n-type layer, a p-type layer/I layer/n-type layer, and a p-type layer/n-type layer.

The intrinsic layer (I layer) may include the compound selected from the compound represented by Chemical Formula 1A, the compound represented by Chemical Formula 1B, and a mixture thereof and the n-type semiconductor compound in a thickness ratio of about 1:100 to about 100:1. The compounds may be included in a thickness ratio ranging from about 1:50 to about 50:1 within the range, for example, about 1:10 to about 10:1, or about 1:1. When the compounds have a composition ratio within the range, an exciton may be effectively produced and a pn junction may be effectively formed.

The p-type layer may include the compound selected from the compound represented by Chemical Formula 1A, the compound represented by Chemical Formula 1B, and a mixture thereof, and the n-type layer may include the n-type semiconductor compound.

The active layer 30 may have a thickness of about 1 nm to about 500 nm, for example, about 5 nm to about 300 nm. When the active layer 30 has a thickness within the range, the active layer may effectively absorb light, effectively separate holes from electrons, and deliver them, thereby effectively improving photoelectronic conversion efficiency. An optimal thickness of a thin film may be, for example, determined by an absorption coefficient of the active layer 30, and may be, for example, a thickness being capable of absorbing light of at least about 70% or more, for example about 80% or more, or about 90%.

In the organic photoelectric device 100, when light enters from the first electrode 10 and/or second electrode 20, and when the active layer 30 absorbs light having a predetermined or given wavelength region, excitons may be produced from the inside. The excitons are separated into holes and electrons in the active layer 30, and the separated holes are transported to an anode that is one of the first electrode 10 and second electrode 20 and the separated electrons are transported to the cathode that is the other of and the first electrode 10 and second electrode 20 so as to flow a current in the organic photoelectric device.

Hereinafter, an organic photoelectric device according to example embodiments is described with reference to FIG. 2.

Figure 2:
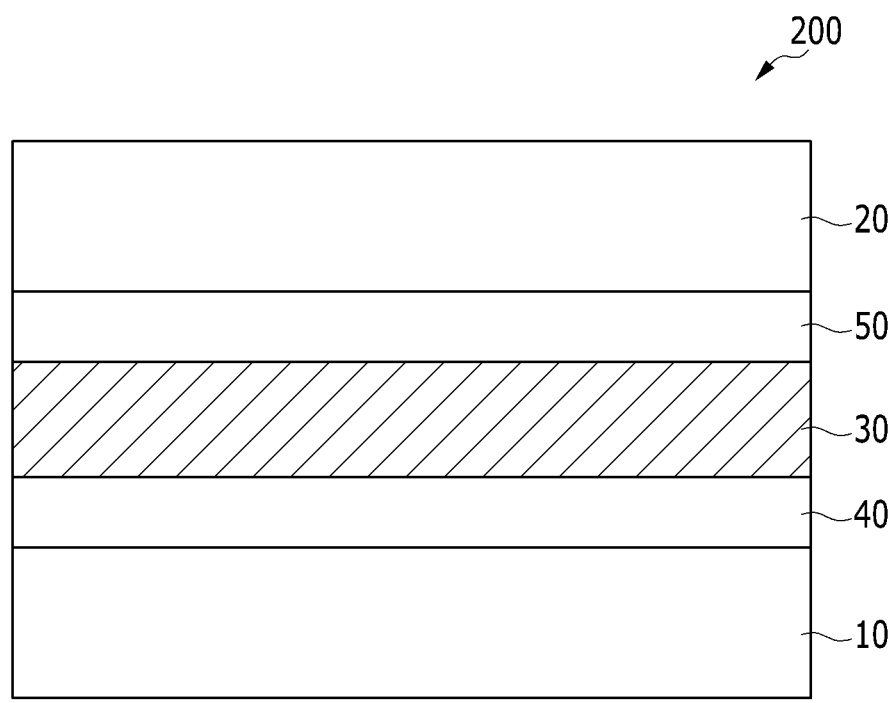
FIG. 2 is a cross-sectional view of an organic photoelectric device according to example embodiments.

FIG. 2 is a cross-sectional view showing an organic photoelectric device according to example embodiments.

Referring to FIG. 2, an organic photoelectric device 200 according to example embodiments includes a first electrode 10 and a second electrode 20 facing each other, and an active layer 30 interposed between the first electrode 10 and the second electrode 20, like the example embodiment illustrated in FIG. 1.

However, the organic photoelectric device 200 according to example embodiments further includes first and second charge auxiliary layers 40 and 50 between the first electrode 10 and the active layer 30, and the second electrode 20 and the active layer 30, unlike the example embodiment illustrated in FIG. 1. The first and second charge auxiliary layers 40 and 50 may facilitate the transfer of holes and electrons separated from the active layer 30, so as to increase efficiency.

The first and second charge auxiliary layers 40 and 50 may be at least one selected from a hole injection layer (HIL) for facilitating hole injection, a hole transport layer (HTL) for facilitating hole transport, an electron blocking layer (EBL) for preventing or inhibiting electron transport, an electron injection layer (EIL) for facilitating electron injection, an electron transport layer (ETL) for facilitating electron transport, and a hole blocking layer (HBL) for preventing or inhibiting hole transport.

The charge auxiliary layers 40 and 50 may include, for example, an organic material, an inorganic material, or an organic/inorganic material. The organic material may be an organic compound having hole or electron characteristics, and the inorganic material may be, for example, a metal oxide (e.g., molybdenum oxide, tungsten oxide, or nickel oxide).

The hole transport layer (HTL) may include one selected from, for example, poly(3,4-ethylenedioxythiophene):poly(styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4,4'-bis[N-(1-naphthyl)-N-phenyl-amino]biphenyl (α-NPD), m-MTDATA, 4,4',4''-tris(N-carbazolyl)-triphenylamine (TCTA), and a combination thereof, but is not limited thereto.

The electron blocking layer (EBL) may include one selected from, for example, poly(3,4-ethylenedioxythiophene):poly(styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4,4'-bis[N-(1-naphthyl)-N-phenyl-amino]biphenyl (α-NPD), m-MTDATA, 4,4',4''-tris(N-carbazolyl)-triphenylamine (TCTA), and a combination thereof, but is not limited thereto.

The electron transport layer (ETL) may include one selected from, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

The hole blocking layer (HBL) may include one selected from, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

Either one of the first and second charge auxiliary layers 40 and 50 may be omitted.

The organic photoelectric device may be applied to various fields, for example, a solar cell, an image sensor, a photo-detector, a photo-sensor, and an organic light emitting diode (OLED), but is not limited thereto.

Hereinafter, an example of an image sensor including the organic photoelectric device is described referring to drawings. As an example of an image sensor, an organic CMOS image sensor is described.

Figure 3:
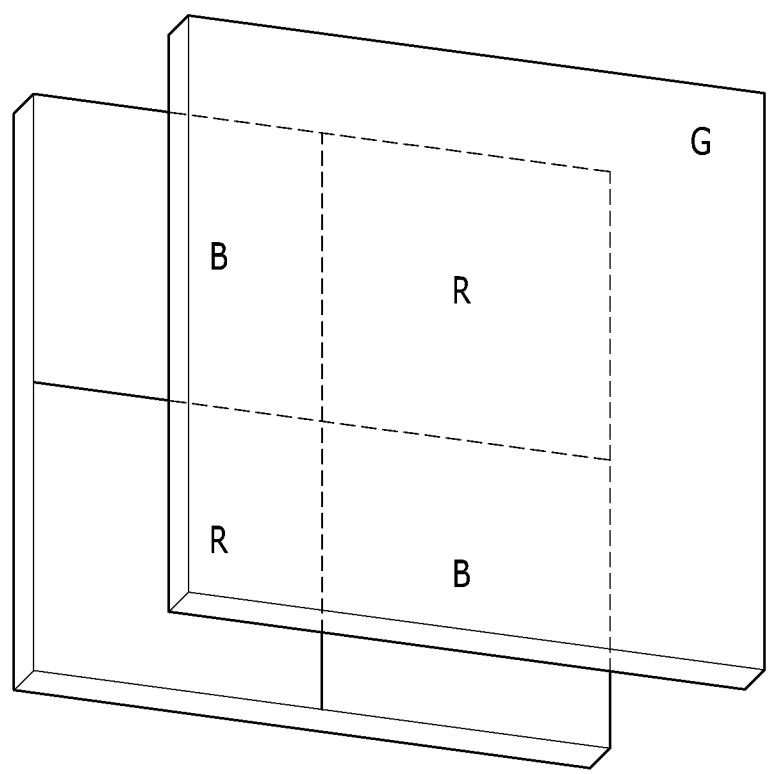
FIG. 3 is a schematic top plan view showing an organic CMOS image sensor according to example embodiments.
Figure 4:
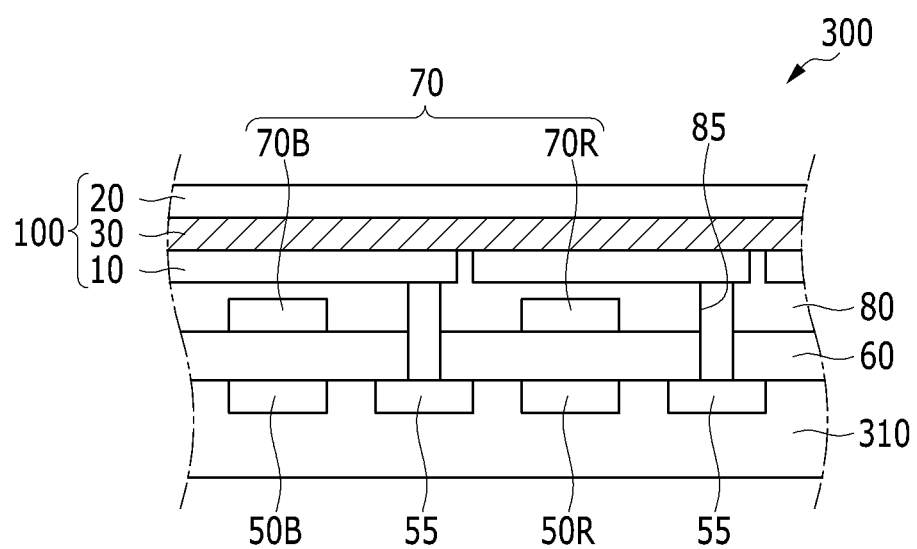
FIG. 4 is a cross-sectional view showing the organic CMOS image sensor of FIG. 3.

FIG. 3 is a schematic top plan view of an organic CMOS image sensor according to example embodiments, and FIG. 4 is a cross-sectional view of the organic CMOS image sensor of FIG. 3.

Referring to FIGS. 3 and 4, an organic CMOS image sensor 300 according to example embodiments includes a semiconductor substrate 310 integrated with photo-sensing devices 50B and 50R, a transmission transistor (not shown), a charge storage device 55, a lower insulation layer 60, a color filter layer 70, an upper insulation layer 80, and an organic photoelectric device 100.

The semiconductor substrate 310 may be a silicon substrate, and is integrated with the photo-sensing devices 50B and 50R, the transmission transistor (not shown), and the charge storage device 55. The photo-sensing devices 50R and 50B may be photodiodes.

The photo-sensing devices 50B and 50R, the transmission transistor, and/or the charge storage device 55 may be integrated in each pixel, and as shown in the drawing, the photo-sensing devices 50B and 50R may be respectively included in a blue pixel and a red pixel and the charge storage device 55 may be included in a green pixel.

The photo-sensing devices 50B and 50R sense light, the information sensed by the photo-sensing devices may be transferred by the transmission transistor, the charge storage device 55 is electrically connected with the organic photoelectric device 100, and the information of the charge storage device 55 may be transferred by the transmission transistor.

In the drawings, the photo-sensing devices 50B and 50R are, for example, arranged in parallel without limitation, and the blue photo-sensing device 50B and the red photo-sensing device 50R may be stacked in a vertical direction.

A metal wire (not shown) and a pad (not shown) are formed on the semiconductor substrate 310. In order to decrease signal delay, the metal wire and pad may be made of a metal having relatively low resistivity, for example, aluminum (Al), copper (Cu), silver (Ag), and alloys thereof, but are not limited thereto. Further, it is not limited to the structure, and the metal wire and pad may be positioned under the photo-sensing devices 50B and 50R.

The lower insulation layer 60 is formed on the metal wire and the pad. The lower insulation layer 60 may be made of an inorganic insulating material such as a silicon oxide and/or a silicon nitride, or a low dielectric constant (low K) material such as SiC, SiCOH, SiCO, and SiOF. The lower insulation layer 60 has a trench exposing the charge storage device 55. The trench may be filled with fillers.

A color filter layer 70 is formed on the lower insulation layer 60. The color filter layer 70 includes a blue filter 70B formed in the blue pixel and a red filter 70R filled in the red pixel. In example embodiments, a green filter is not included, but a green filter may be further included.

The color filter layer 70 may be omitted. For example, when the blue photo-sensing device 50B and the red photo-sensing device 50R are stacked in a vertical direction, the blue photo-sensing device 50B and the red photo-sensing device 50R may selectively absorb light in each wavelength region depending on their stack depth, and the color filter layer 70 may not be equipped.

The upper insulation layer 80 is formed on the color filter layer 70. The upper insulation layer 80 eliminates a step caused by the color filter layer 70 and smoothes the surface. The upper insulation layer 80 and the lower insulation layer 60 may include a contact hole (not shown) exposing a pad, and a through-hole 85 exposing the charge storage device 55 of the green pixel.

The organic photoelectric device 100 is formed on the upper insulation layer 80. The organic photoelectric device 100 includes the first electrode 10, the active layer 30, and the second electrode 20 as described above.

The first electrode 10 and the second electrode 20 may be transparent electrodes, and the active layer 30 is the same as described above. The active layer 30 selectively absorbs light in a green wavelength region and replaces a color filter of a green pixel.

When light enters from the second electrode 20, the light in a green wavelength region may be mainly absorbed in the active layer 30 and photoelectronically converted, while the light in the rest of the wavelength region passes through first electrode 10 and may be sensed in the photo-sensing devices 50B and 50R.

As described above, the organic photoelectric device selectively absorbing light in a green wavelength region is stacked, and thereby a size of an image sensor may be decreased and a down-sized image sensor may be realized.

Figure 5:
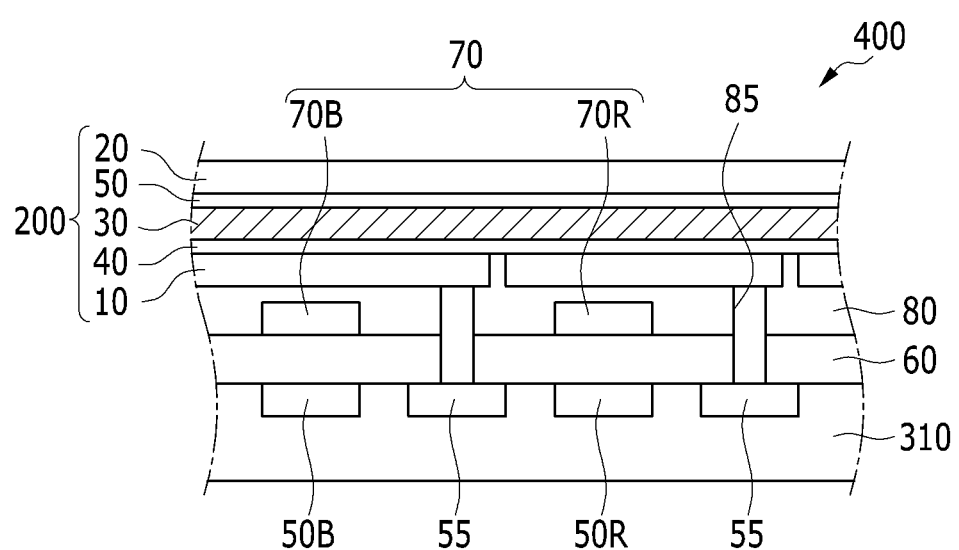
FIG. 5 is a schematic cross-sectional view showing an organic CMOS image sensor according to example embodiments.

In FIG. 4, the organic photoelectric device 100 of FIG. 1 is included, but it is not limited thereto, and thus the organic photoelectric device 200 of FIG. 2 may be applied in the same manner. FIG. 5 shows a structure of an image sensor having such a structure, and is a cross-sectional view of an organic CMOS image sensor 400 including the organic photoelectric device 200 in FIG. 2.

Figure 6:
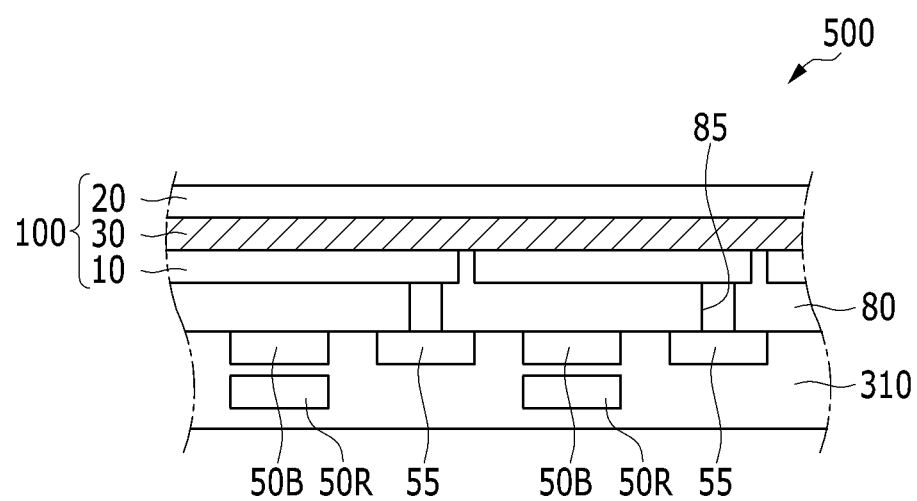
FIG. 6 is a schematic cross-sectional view showing an organic CMOS image sensor according to example embodiments.

FIG. 6 is a cross-sectional view showing the organic CMOS image sensor according to example embodiments.

The organic CMOS image sensor 500 according to example embodiments includes a semiconductor substrate 310 integrated with photo-sensing devices 50B and 50R, a transmission transistor (not shown), a charge storage device 55, an insulation layer 80, and an organic photoelectric device 100, like the example embodiment illustrated in FIGS. 3 and 4.

However, the organic CMOS image sensor 500 according to example embodiments includes the blue photo-sensing device 50B and the red photo-sensing device 50R that are stacked and does not include a color filter layer 70, unlike the example embodiment illustrated in FIGS. 3 and 4. The blue photo-sensing device 50B and the red photo-sensing device 50R are electrically connected with the charge storage (not shown), and the information of the charge storage device 55 may be transferred by the transmission transistor. The blue photo-sensing device 50B and the red photo-sensing device 50R may selectively absorb light in each wavelength region depending on a stack depth.

As described above, the organic photoelectric device selectively absorbing light in a green wavelength region is stacked and the red photo-sensing device and the blue photo-sensing device are stacked, and thereby a size of an image sensor may be decreased and a down-sized image sensor may be realized. As described above, the organic photoelectric device 100 has improved green wavelength selectivity, and crosstalk caused by unnecessary absorption of light in a wavelength region except green may be decreased while increasing sensitivity.

In FIG. 6, the organic photoelectric device 100 of FIG. 1 is included, but it is not limited thereto, and thus the organic photoelectric device 200 of FIG. 2 may be applied in the same manner.

Figure 7:
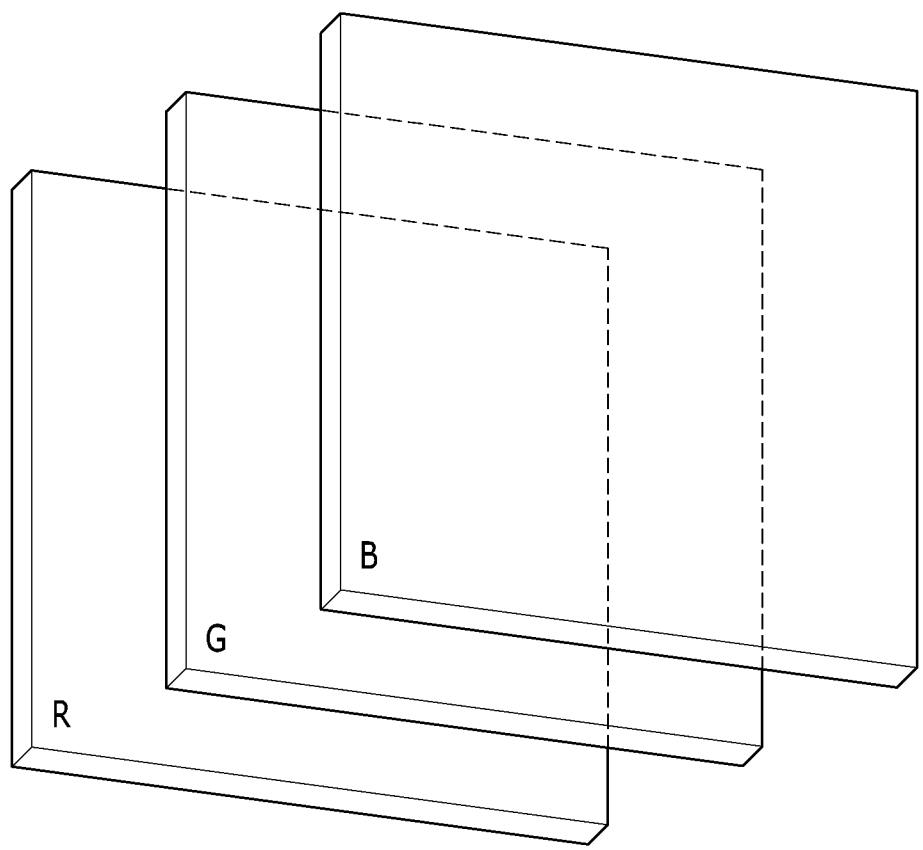
FIG. 7 is a schematic view showing an organic CMOS image sensor according to example embodiments.

FIG. 7 is a schematic view showing an organic CMOS image sensor according to example embodiments.

Referring to FIG. 7, the organic CMOS image sensor according to example embodiments includes a green photoelectric device (G) selectively absorbing light in a green wavelength region, a blue photoelectric device (B) selectively absorbing light in a blue wavelength region, and a red photoelectric device (R) selectively absorbing light in a red wavelength region that are stacked.

In the drawing, the red photoelectric device (R), the green photoelectric device (G), and the blue photoelectric device (B) are sequentially stacked, but the stack order may be changed without limitation.

The green photoelectric device may be the above organic photoelectric device 100, the blue photoelectric device may include electrodes facing each other and an active layer interposed therebetween and including an organic material selectively absorbing light in a blue wavelength region, and the red photoelectric device may include electrodes facing each other and an active layer interposed therebetween and including an organic material selectively absorbing light in a red wavelength region.

As described above, the organic photoelectric device selectively absorbing light in a green wavelength region, the organic photoelectric device selectively absorbing light in a red wavelength region, and the organic photoelectric device selectively absorbing light in a blue wavelength region are stacked, and thereby a size of an image sensor may be decreased and a down-sized image sensor may be realized.

The image sensor may be applied to various electronic devices, for example, a mobile phone and a digital camera, but is not limited thereto.

Hereinafter, the present disclosure is illustrated in more detail with reference to examples. However, these are examples, and the present disclosure is not limited thereto.

SYNTHESIS EXAMPLES

Synthesis Example 1

A compound represented by the following Chemical Formula 1-1 is synthesized according to Reaction Scheme 1-1.

[Chemical Formula 1-1]

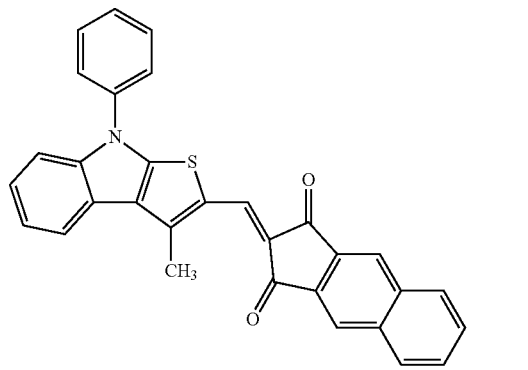

[Reaction Scheme 1-1]

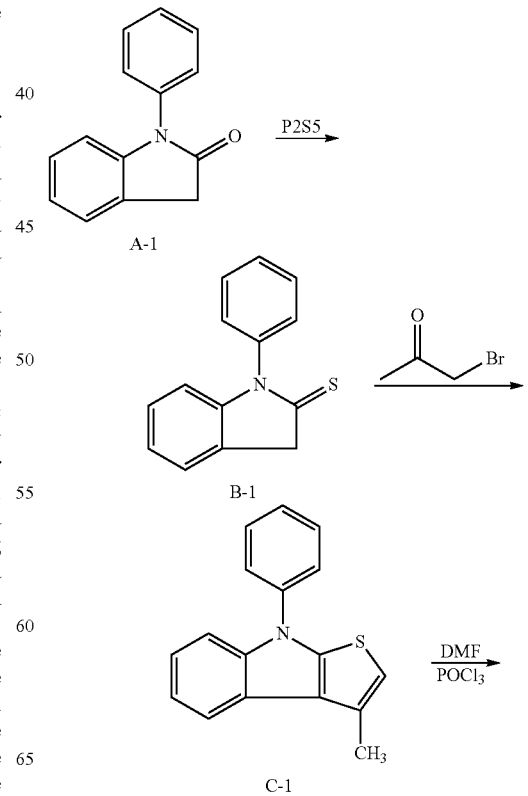

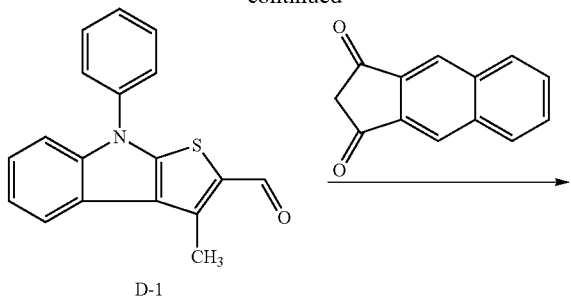

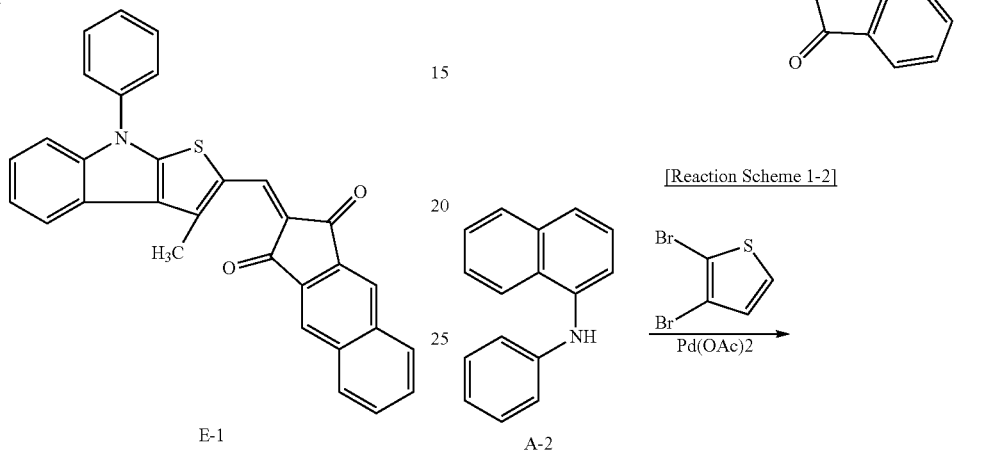

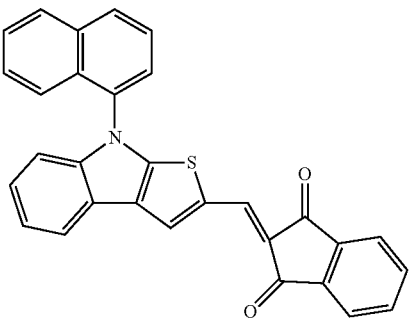

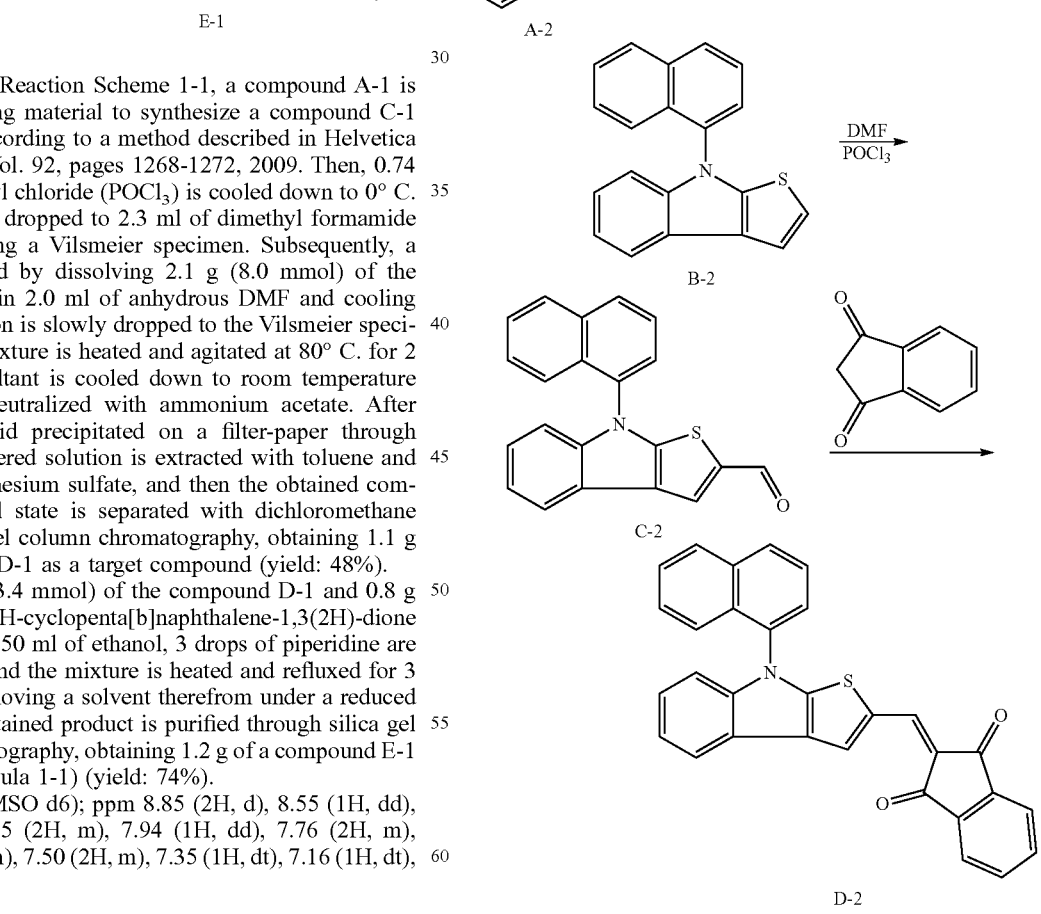

As shown in Reaction Scheme 1-1, a compound A-1 is used as a starting material to synthesize a compound C-1 (yield: 53%) according to a method described in Helvetica Chemica Acta Vol. 92, pages 1268-1272, 2009. Then, 0.74 ml of phosphoryl chloride ($POCl_3$) is cooled down to 0° C. and then slowly dropped to 2.3 ml of dimethyl formamide (DMF), preparing a Vilsmeier specimen. Subsequently, a product obtained by dissolving 2.1 g (8.0 mmol) of the compound C-1 in 2.0 ml of anhydrous DMF and cooling down the solution is slowly dropped to the Vilsmeier specimen, and the mixture is heated and agitated at 80° C. for 2 hours. The resultant is cooled down to room temperature (25° C.) and neutralized with ammonium acetate. After removing a solid precipitated on a filter-paper through filtering, the filtered solution is extracted with toluene and dried with magnesium sulfate, and then the obtained compound in an oil state is separated with dichloromethane through silica gel column chromatography, obtaining 1.1 g of a compound D-1 as a target compound (yield: 48%).

Then, 1.0 g (3.4 mmol) of the compound D-1 and 0.8 g (4.1 mmol) of 1H-cyclopenta[b]naphthalene-1,3(2H)-dione are dissolved in 50 ml of ethanol, 3 drops of piperidine are added thereto, and the mixture is heated and refluxed for 3 hours. After removing a solvent therefrom under a reduced pressure, the obtained product is purified through silica gel column chromatography, obtaining 1.2 g of a compound E-1 (Chemical Formula 1-1) (yield: 74%).

$^1$H NMR (DMSO d6); ppm 8.85 (2H, d), 8.55 (1H, dd), 8.46 (1H,s), 8.15 (2H, m), 7.94 (1H, dd), 7.76 (2H, m), 7.58-7.62 (3H, m), 7.50 (2H, m), 7.35 (1H, dt), 7.16 (1H, dt), 2.65 (3H,s).

Synthesis Example 2

A compound represented by the following Chemical Formula 1-2 is synthesized according to Reaction Scheme 1-2.

As shown in Reaction Scheme 1-2, a compound B-2 is synthesized by using 1-naphthylphenylamine and 2,3-dibromothiophene referring to Angewante Chem., Int. Ed. 2007, 46, 1627-1629. Then, a compound C-2 is synthesized according to the same method as the method of synthesizing the compound D-1 represented by Reaction Scheme 1-1. 1.0 g (3.1 mmol) of the compound C-2 and 0.6 g (4.1 mmol) of 5,6-dihydro-1H-indene-1,3(2H)-dione are dissolved in 50 ml of ethanol, three drops of piperidine are added thereto, and the mixture is heated and refluxed for 3 hours. After removing a solvent therefrom under a reduced pressure, the obtained product is purified through silica gel column chromatography, obtaining 1.1 g of a compound D-2 (Chemical Formula 1-2) (yield: 78%).

$^1$H NMR (DMSO d6); ppm 8.55 (1H, dd), 8.46 (1H,s), 8.15-8.11 (3H, m), 7.94-7.93 (3H, m), 7.9 (1H,s), 7.79 (1H, t), 7.71 (2H, m), 7.60-7.52 (3H, m), 7.35 (1H, dt), 7.16 (1H, dt).

Synthesis Example 3

A compound represented by the following Chemical Formula 1-3 is synthesized according to Reaction Scheme 1-3.

[Chemical Formula 1-3]

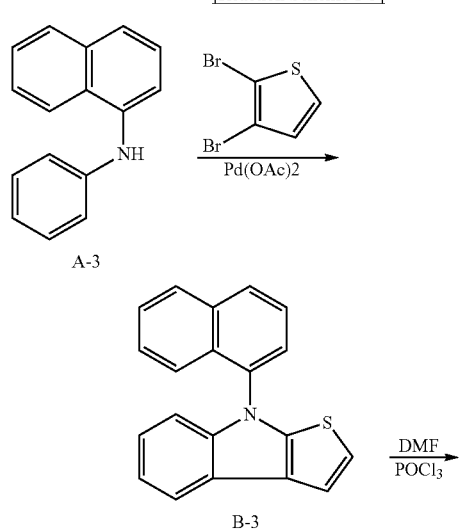

[Reaction Scheme 1-3]

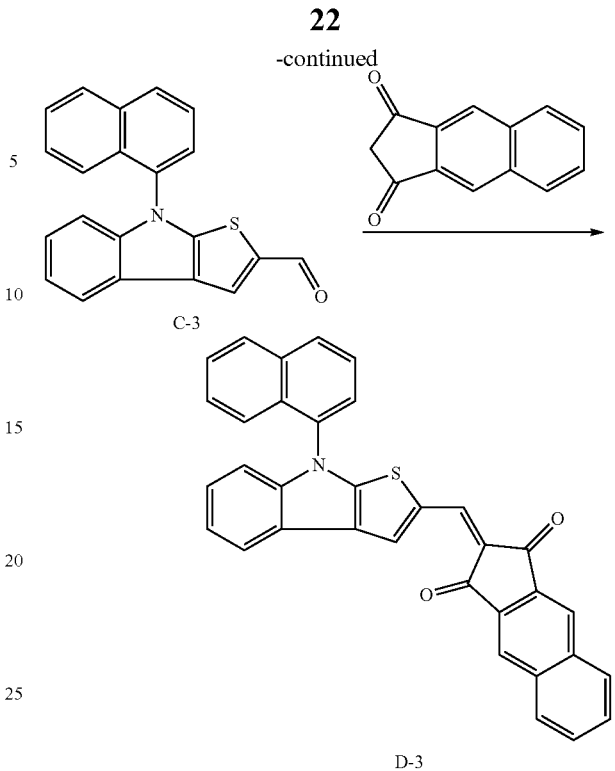

As shown in Reaction Scheme 1-3, a compound B-3 is synthesized by using 1-naphthylphenylamine and 2,3-dibromothiophene according to the same method as the method as described in Angewante Chem., Int. Ed. 2007, 46, 1627-1629. Then, a compound C-3 is synthesized according to the same method as the method of synthesizing the compound D-1 represented by Reaction Scheme 1-1. 1.0 g (3.1 mmol) of the compound C-3 and 0.9 g (4.7 mmol) of 1H-cyclopenta[b]naphthalene-1,3(2H)-dione are dissolved in 50 ml of ethanol, three drops of piperidine are added thereto, and the mixture is heated and refluxed for 3 hours. After removing a solvent therefrom under a reduced pressure, the obtained product is purified through silica gel column chromatography, obtaining 1.0 g of a compound D-3 (Chemical Formula 1-3) (yield: 75%).

$^1$H NMR (DMSO d6); ppm 8.85 (2H,s), 8.55 (1H, dd), 8.46 (1H,s), 8.15-8.11 (5H, m), 7.94 (1H, dd), 7.9 (1H,s), 7.79-7.76 (3H, m), 7.60-7.52 (3H, m), 7.35 (1H, dt), 7.16 (1H, dt).

Comparative Synthesis Example 1

A compound represented by the following Chemical Formula 1-4 is prepared.

[Chemical Formula 1-4]

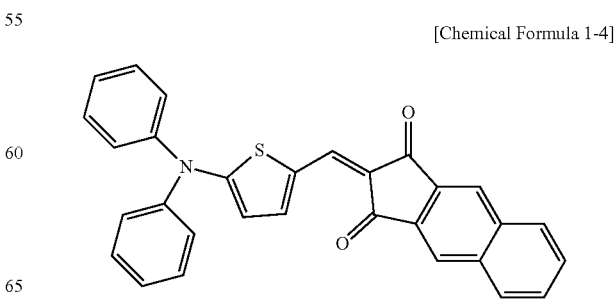

Comparative Synthesis Example 2

A compound represented by the following Chemical Formula 1-5 is prepared.

[Chemical Formula 1-5]

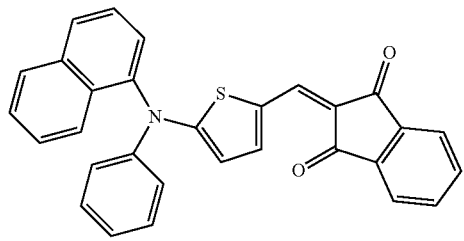

Comparative Synthesis Example 3

A compound represented by the following Chemical Formula 1-6 is synthesized according to Reaction Scheme 1-4.

[Chemical Formula 1-6]

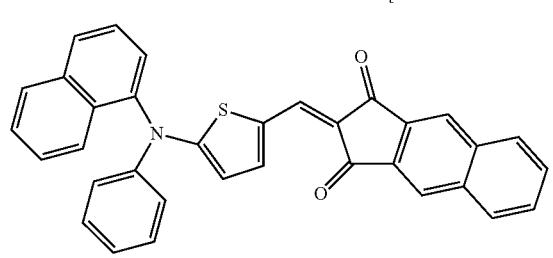

[Reaction Scheme 1-4]

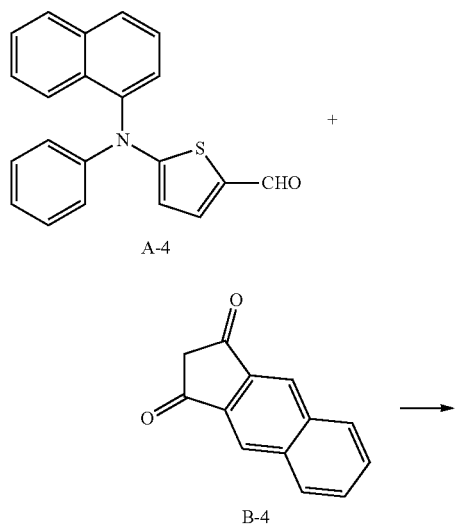

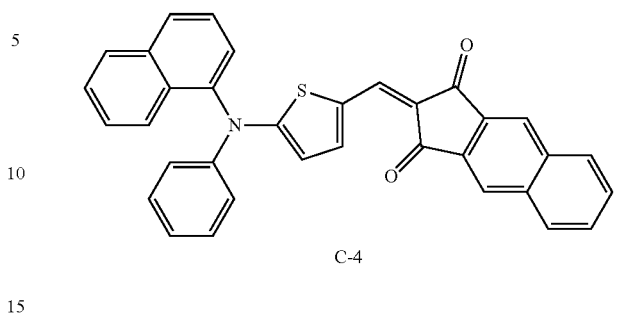

C-4

As shown in Reaction Scheme 1-4, 5 g (15.18 mmol) of the compound A-4 and 3.425 g (17.46 mmol) of the compound B-4 are put in a 3-necked round-bottomed flask, dried for 8 hours and then purged with $N_2$ gas. Then, 100 ml of ethanol and piperidine are added to the reactant in a dropwise fashion, and the mixture is refluxed at a temperature ranging from 75 to 80° C. for 6 hours. The resultant is cooled down to room temperature of 25° C., and water is added thereto. When powder is formed therein, the powder is filtered and purified through column chromatography (developing solvent: dichloromethane/hexane/ethylacetate). Then, dichloromethane and hexane are used for recrystallization, obtaining 6.2 g of a compound C-4 (Chemical Formula 1-6) (yield: 80%).

Thermal Stability of Compounds According to Synthesis Examples 1 to 3 and Comparative Synthesis Examples 1 to 3

The melting point of each compound according to Synthesis Examples 1 to 3 and Comparative Synthesis Examples 1 to 3, the temperature of a crucible used for deposition, and a temperature difference (ΔT) between the melting point and the crucible temperature are measured. The results are provided in the following Table 1.

Light Absorption Characteristics of Compounds According to Synthesis Examples 1 to 3 and Comparative Synthesis Examples 1 to 3

Each compound according to Synthesis Examples 1 to 3 and Comparative Synthesis Examples 1 to 3 is thermally deposited under a high degree of vacuum ($<10^{-7}$ Torr) at a speed of 1.0 Å/s to form a 70 nm-thick thin film, and the thin film is radiated by ultraviolet (UV)-visible rays (UV-Vis) with a Cary 5000 UV spectroscope (manufactured by Varian). The maximum absorption wavelength of the thin film formed of each compound according to Synthesis Examples 1 to 3 and Comparative Synthesis Examples 1 to 3 is measured by using a UV-2450 UV-Visible Spectrophotometer (manufactured by Shimadzu), and its full width at half maximum (FWHM) is obtained by measuring a half of the maximum absorption height of the obtained spectrum.

TABLE 1

| | Melting point (° C.) | Crucible temperature at deposition (° C.) | ΔT (° C.) | HOMO (eV) | LUMO (eV) | $\lambda_{max}$ (nm) | FWHM (nm) |
|---|---|---|---|---|---|---|---|
| Synthesis Example 1 | 330 | 260 | 70 | 5.3 | 3.3 | 520 | 94 |
| Synthesis Example 2 | 285 | 225 | 50 | 5.4 | 3.5 | 528 | 89 |
| Synthesis Example 3 | 335 | 270 | 65 | 5.5 | 3.6 | 540 | 80 |
| Comparative Synthesis Example 1 | 240 | 242 | 2 | 5.3 | 3.1 | 518 | 92 |
| Comparative Synthesis Example 2 | 300 | 265 | 35 | 5.4 | 3.2 | 526 | 88 |
| Comparative Synthesis Example 3 | 304 | 272 | 32 | 5.5 | 3.5 | 566 | 80 |

Referring to the Table 1, the compounds of Synthesis Examples 1 to 3 have a high melting point and thus show a temperature difference (ΔT) of greater than or equal to 50° C. from their crucible temperatures compared with the compounds of Comparative Synthesis Examples 1 to 3. Specifically, the compounds of Synthesis Examples 1 to 3 show higher ΔT than the compounds of Comparative Synthesis Examples 1 to 3 when comparing Synthesis Example 1 with Comparative Synthesis Example 1, Synthesis Example 2 with Comparative Synthesis Example 2, and Synthesis Example 3 with Comparative Synthesis Example 3 having the same structure except for connection of a benzene ring to a thiophene ring. Accordingly, the compounds of Synthesis Examples 1 to 3 may be stably deposited and thus show improved mass-production applicability. In addition, the compounds show a maximum absorption wavelength of 500 nm to 600 nm and may selectively absorb a wavelength in a green region.

Manufacture of Organic Photoelectric Device

Example 1

An about 100 nm-thick anode is formed by sputtering ITO on a glass substrate, and a 10 nm-thick molybdenum oxide ($MoO_x$, 0<x≤3) thin film is laminated as a charge auxiliary layer thereon. Subsequently, an 85 nm-thick active layer is formed by codepositing the compound of Synthesis Example 1 (a p-type semiconductor compound) and C60 (an n-type semiconductor compound) in a thickness ratio of 1:1 on the molybdenum oxide ($MoO_x$) thin film. On the active layer, a 70 nm-thick cathode is formed by sputtering aluminum (Al), manufacturing an organic photoelectric device.

Example 2

An organic photoelectric device is manufactured according to the same method as Example 1, except for using the p-type semiconductor compound of Synthesis Example 2 instead of the p-type semiconductor compound of Synthesis Example 1.

Example 3

An organic photoelectric device is manufactured according to the same method as Example 1, except for using the p-type semiconductor compound of Synthesis Example 3 instead of the p-type semiconductor compound of Synthesis Example 1.

Comparative Example 1

An organic photoelectric device is manufactured according to the same method as Example 1, except for using the p-type semiconductor compound of Comparative Synthesis Example 1 instead of the p-type semiconductor compound of Synthesis Example 1.

Comparative Example 2

An organic photoelectric device is manufactured according to the same method as Example 1, except for using the p-type semiconductor compound of Comparative Synthesis Example 2 instead of the p-type semiconductor compound of Synthesis Example 1.

Comparative Example 3

An organic photoelectric device is manufactured according to the same method as Example 1, except for using the p-type semiconductor compound of Comparative Synthesis Example 3 instead of the p-type semiconductor compound of Synthesis Example 1.

External Quantum Efficiency (EQE)

External quantum efficiency (EQE) of the organic photoelectric devices according to Examples 1 to 3 and Comparative Examples 1 to 3 depending on a wavelength and a voltage is evaluated.

The external quantum efficiency is measured by using an IPCE measurement system (McScience Co., Ltd. Korea). First of all, the IPCE measurement system is calibrated by using a Si photodiode (Hamamatsu Photonics K.K., Japan), the organic photoelectric devices of Examples 1 to 3 and Comparative Examples 1 to 3 are then respectively mounted thereon, and their external quantum efficiency in a wavelength region of about 300 to 700 nm is determined.

When an organic photoelectric device manufactured in a first deposition process has EQE of 100%, the relative EQE of an organic photoelectric device manufactured in a third deposit process is measured and provided in the following Table 2.

TABLE 2

| | EQE decrease ratio (%) |
|---|---|
| Example 1 | 99 |
| Example 2 | 99 |
| Example 3 | 100 |
| Comparative Example 1 | 83 |
| Comparative Example 2 | 80 |
| Comparative Example 3 | 74 |

Referring to the Table 2, the organic photoelectric devices according to Examples 1 to 3 show a smaller EQE decrease ratio compared with the organic photoelectric devices according to Comparative Examples 1 to 3.

While this disclosure has been described in connection with what is presently considered to be practical example embodiments, it is to be understood that the inventive concepts are not limited to the disclosed embodiments, but, on the contrary, is intended to cover various modifications and equivalent arrangements included within the spirit and scope of the appended claims.

What is claimed is:

1. A compound for an organic photoelectric device represented by the following Chemical Formula 1A or 1B:

[Chemical Formula 1A]

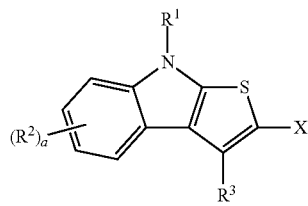

[Chemical Formula 1B]

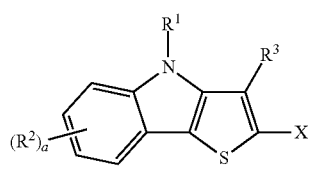

wherein, in Chemical Formulae 1A and 1B,
each of $R^1$ to $R^3$ are independently one of hydrogen and a monovalent organic group,
a is an integer of 0 to 4, and
X is represented by Chemical Formula 2:

[Chemical Formula 2]

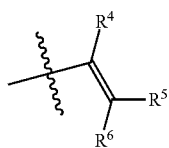

wherein, in Chemical Formula 2,
$R^4$ is one of hydrogen and a monovalent organic group, and
$R^5$ and $R^6$ form a heteroatom-containing ring having electron withdrawing properties.

2. The compound of claim 1, wherein the heteroatom-containing ring is one of substituents represented by the following Chemical Formulae 1a to 1e:

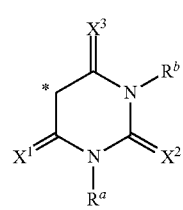

where * indicates a position bound to a methine group of Chemical Formula 2,
each of $R^a$, $R^b$, and $R^c$ are independently one of hydrogen and a monovalent organic group,
each of $X^1$ to $X^{10}$ are independently one of O and S,
each of $Y^1$ and $Y^2$ are independently one of S and CRR' wherein each of R and R' are independently one of hydrogen, CN, and a $C_1$ to $C_{10}$ alkyl group,
m is an integer of 1 to 3, and
n is an integer of 0 or 1.

3. The compound of claim 2, wherein in Chemical Formulae 1A, 1B, and 1a to 1e, the monovalent organic group is one of a substituted or unsubstituted $C_1$ to $C_{30}$ alkyl group, a substituted or unsubstituted $C_1$ to $C_{30}$ alkoxy group, a substituted or unsubstituted $C_4$ to $C_{30}$ cycloalkyl group, a substituted or unsubstituted $C_6$ to $C_{30}$ aryl group, a substituted or unsubstituted $C_3$ to $C_{30}$ heterocycloalkyl group, a substituted or unsubstituted $C_3$ to $C_{30}$ heteroaryl group, an amine group, a substituted or unsubstituted $C_1$ to $C_{30}$ alkylamine group, a substituted or unsubstituted $C_6$ to $C_{30}$ arylamine group, a substituted or unsubstituted silyl group, a substituted or unsubstituted $C_6$ to $C_{30}$ aryloxy group, a thiol group, a substituted or unsubstituted $C_1$ to $C_{30}$ alkylthio group, a substituted or unsubstituted $C_6$ to $C_{30}$ arylthio group, a cyano group, a cyano-containing group, a halogen, a halogen-containing group, a substituted or unsubstituted sulfonyl group, a substituted or unsubstituted aminosulfonyl group, a substituted or unsubstituted arylsulfonyl group, and a combination thereof.

4. The compound of claim 2, wherein in Chemical Formulae 1a to 1e, the monovalent organic group is one of a substituted or unsubstituted $C_1$ to $C_{30}$ alkyl group, a substituted or unsubstituted $C_1$ to $C_{30}$ alkoxy group, a substituted or unsubstituted $C_4$ to $C_{30}$ cycloalkyl group, a substituted or unsubstituted $C_6$ to $C_{30}$ aryl group, a substituted or unsubstituted $C_3$ to $C_{30}$ heterocycloalkyl group, a substituted or unsubstituted $C_3$ to $C_{30}$ heteroaryl group, an amine group, a substituted or unsubstituted $C_1$ to $C_{30}$ alkylamine group, a substituted or unsubstituted $C_6$ to $C_{30}$ arylamine group, a substituted or unsubstituted silyl group, a substituted or unsubstituted $C_6$ to $C_{30}$ aryloxy group, a thiol group, a substituted or unsubstituted $C_1$ to $C_{30}$ alkylthio group, a substituted or unsubstituted $C_6$ to $C_{30}$ arylthio group, a cyano group, a cyano-containing group, a halogen, a halogen-containing group, a substituted or unsubstituted sulfonyl group, a substituted or unsubstituted aminosulfonyl group, a substituted or unsubstituted arylsulfonyl group, and a combination thereof.

5. The compound of claim 1, wherein the compound is represented by the following Chemical Formula 3A or Chemical Formula 3B:

[Chemical Formula 3A]

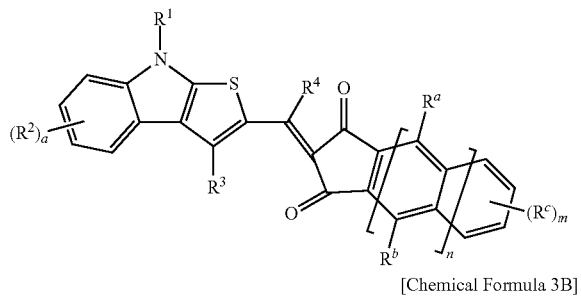

[Chemical Formula 3B]

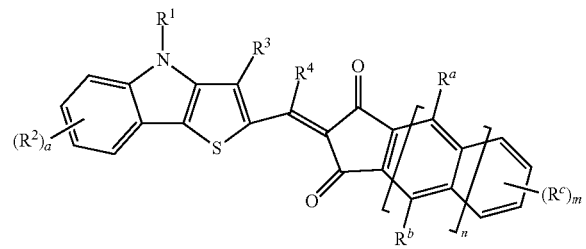

wherein, in Chemical Formulae 3A and 3B,
each of $R^1$ to $R^3$ are independently one of hydrogen and a monovalent organic group,
a is an integer of 0 to 4,
each of $R^a$, $R^b$, and $R^c$ are independently one of hydrogen and a monovalent organic group,
m is an integer of 1 to 3, and
n is an integer of 0 or 1.

6. The compound of claim 1, wherein the compound has a maximum absorption wavelength ($\lambda_{max}$) at about 500 nm to about 600 nm.

7. The compound of claim 1, wherein the compound shows a light absorption curve having a full width at half maximum (FWHM) in a thin film state of about 50 nm to about 100 nm.

8. The compound of claim 1, wherein the compound is a p-type semiconductor compound.

9. The compound of claim 1, wherein the compound has a higher melting point by about 50° C. or greater than a deposition temperature.

10. An organic photoelectric device comprising:
a first electrode and a second electrode facing each other, and
an active layer between the first electrode and the second electrode, wherein the active layer includes the compound of claim 1.

11. The organic photoelectric device of claim 10, wherein the active layer further comprises a n-type semiconductor compound.

12. The organic photoelectric device of claim 11, wherein the n-type semiconductor compound is one of a sub-phthalocyanine, fullerene or a fullerene derivative, thiophene or a thiophene derivative, and a combination thereof.

13. The organic photoelectric device of claim 11, wherein the active layer comprises the compound represented by Chemical Formula 1A, the compound represented by Chemical Formula 1B, or a mixture thereof.

14. The organic photoelectric device of claim 11, wherein the active layer further comprises at least one of a p-type layer on one side of an intrinsic layer and a n-type layer on the other side of the intrinsic layer.

15. The organic photoelectric device of claim 11, wherein the compound represented by Chemical Formula 1A or 1B is a first p-type semiconductor compound, and the active layer further comprises a second p-type semiconductor compound selectively absorbing green light.

16. An image sensor comprising the organic photoelectric device of claim 10.

17. The image sensor of claim 16, further comprising:
a semiconductor substrate integrated with a plurality of first photo-sensing devices sensing light in a blue wavelength region and a plurality of second photo-sensing devices sensing light in a red wavelength region, and
the organic photoelectric device on the semiconductor substrate is configured to selectively absorb light in a green wavelength region.

18. The image sensor of claim 17, wherein the first photo-sensing devices and the second photo-sensing devices are stacked in a vertical direction on the semiconductor substrate.

19. The image sensor of claim 17, further comprising:
a color filter layer between the semiconductor substrate and the organic photoelectric device, wherein the color filter layer includes a blue filter configured to selectively absorb light in a blue wavelength region and a red filter configured to selectively light in a red wavelength region.

20. The image sensor of claim 16, wherein
the organic photoelectric device is a green photoelectric device, and
the green photoelectric device, a blue photoelectric device configured to selectively absorb light in a blue wavelength region, and a red photoelectric device configured to selectively absorb light in a red wavelength region are stacked.

21. An electronic device comprising the image sensor of claim 16.

* * * * *